United States Patent
Bharat et al.

(10) Patent No.: US 11,197,721 B2
(45) Date of Patent: Dec. 14, 2021

(54) ULTRASOUND TRACKING APPARATUS FOR DISPOSABLE BIOPSY NEEDLES

(71) Applicant: KONINKLIJKE PHILIPS N.V., Eindhoven (NL)

(72) Inventors: Shyam Bharat, Arlington, MA (US); Ramon Quido Erkamp, Swampscott, MA (US); Ameet Kumar Jain, Boston, MA (US); Francois Guy Gerard Marie Vignon, Andover, MA (US)

(73) Assignee: KONINKLIKE PHILIPS N.V., Eindhoven (NL)

(*) Notice: Subject to any disclaimer, the term of this patent is extended or adjusted under 35 U.S.C. 154(b) by 412 days.

(21) Appl. No.: 15/324,137

(22) PCT Filed: Jul. 15, 2015

(86) PCT No.: PCT/IB2015/055352
§ 371 (c)(1),
(2) Date: Jan. 5, 2017

(87) PCT Pub. No.: WO2016/009366
PCT Pub. Date: Jan. 21, 2016

(65) Prior Publication Data
US 2017/0245941 A1    Aug. 31, 2017

Related U.S. Application Data

(60) Provisional application No. 62/025,480, filed on Jul. 16, 2014.

(51) Int. Cl.
*A61B 34/20* (2016.01)
*A61B 90/00* (2016.01)
*A61B 10/02* (2006.01)
*A61B 17/00* (2006.01)
*A61B 17/34* (2006.01)

(52) U.S. Cl.
CPC .......... *A61B 34/20* (2016.02); *A61B 10/0275* (2013.01); *A61B 90/37* (2016.02); *A61B 2017/0023* (2013.01); *A61B 2017/00473* (2013.01); *A61B 2017/3413* (2013.01); *A61B 2034/2063* (2016.02); *A61B 2090/378* (2016.02); *A61B 2090/3788* (2016.02); *A61B 2090/3925* (2016.02)

(58) Field of Classification Search
None
See application file for complete search history.

(56) References Cited

U.S. PATENT DOCUMENTS 8,764,680 B2    7/2014    Rhad et al.
9,414,816 B2    8/2016    Rhad et al.
(Continued)

FOREIGN PATENT DOCUMENTS

CN    102860841 A    1/2013

*Primary Examiner* — Ankit D Tejani

(57) ABSTRACT

A system for tracking a medical device includes an introducer. Two or more sensors are disposed along a length of the introducer and are spaced apart along the length. An interface is configured to connect to the introducer such that the introducer and the interface operatively couple to and support the medical device wherein the two or more sensors are configured to provide feedback for positioning and orienting the medical device using medical imaging.

20 Claims, 4 Drawing Sheets

(56) References Cited

U.S. PATENT DOCUMENTS

| | | |
|---|---|---|
| 9,421,002 B2 | 8/2016 | Heske et al. |
| 9,456,806 B2 | 10/2016 | Chudzik et al. |
| 9,554,716 B2 | 1/2017 | Burnside et al. |
| 2009/0247900 A1 | 10/2009 | Zimmer |
| 2010/0204569 A1 | 8/2010 | Burnside |
| 2011/0015490 A1 | 1/2011 | Trovato et al. |
| 2012/0316558 A1 | 12/2012 | Hendriks |
| 2012/0330186 A1 | 12/2012 | Rhad |
| 2014/0024928 A1 | 1/2014 | Boctor |
| 2014/0316299 A1* | 10/2014 | Burdorff ............ A61B 10/0266 600/567 |
| 2015/0051482 A1 | 2/2015 | Liu et al. |

* cited by examiner

ULTRASOUND TRACKING APPARATUS FOR DISPOSABLE BIOPSY NEEDLES

CROSS-REFERENCE TO PRIOR APPLICATIONS

This application is the U.S. National Phase application under 35 U.S.C. § 371 of International Application No. PCT/IB2015/055352, filed on Jul. 15, 2015, which claims the benefit of U.S. Provisional Patent Application No. 62/025,480, filed on Jul. 16, 2014. These applications are hereby incorporated by reference herein.

BACKGROUND

Technical Field

This disclosure relates to medical instruments and more particularly to a system and method to track a needle under ultrasound guidance having dedicated hardware to enable cost-effective tracking.

Description of the Related Art

A biopsy can be described as a minimally invasive procedure where a sample of tissue is obtained for ex vivo pathologic analysis. Typically, a biopsy device (or biopsy gun) can comprise an inner stylet and outer hollow cannula, both of which can be attached to the biopsy gun handle. In many instances, the biopsy gun can be a disposable device. A typical biopsy device can be positioned in tissue under some form of image guidance (typically ultrasound (US)) and then 'fired'. The act of firing generally first deploys the inner stylet and then the outer cannula in quick succession, thus capturing a tissue sample in the slot of the inner stylet. The actual location of the biopsy sample can be offset from the resting position of the biopsy device prior to firing.

In many biopsy procedures, disposable biopsy guns are employed. Since these are typically designed for one-time use only, incorporating ultrasound sensing technology along with its amplifying and noise-cancelling electronics on these guns can be complex and relatively expensive.

SUMMARY

In accordance with the present principles, a system for tracking a medical device includes an introducer. Two or more sensors are disposed along a length of the introducer and are spaced apart along the length. An interface is configured to connect to the introducer such that the introducer and the interface operatively couple to and support the medical device wherein the two or more sensors are configured to provide feedback for positioning and orienting the medical device using medical imaging.

Another system for tracking a medical device includes an introducer, and two or more sensors disposed along a length of the introducer and being spaced apart along the length. An interface is configured to connect to the introducer such that the introducer and the interface operatively couple to and support the medical device wherein the two or more sensors are configured to provide feedback for positioning and orienting the medical device. An interpretation module is configured to receive the feedback and generate image information for indicating a position and orientation of the introducer in an image.

A method for tracking a medical device includes providing an introducer with two or more sensors disposed along a length of the introducer and being spaced apart along the length, the introducer being coupled to an interface; operatively supporting the medical device by the introducer and the interface; and receiving signals from a subject by the two or more sensors which are configured to provide feedback for positioning and orienting the medical device in a medical image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
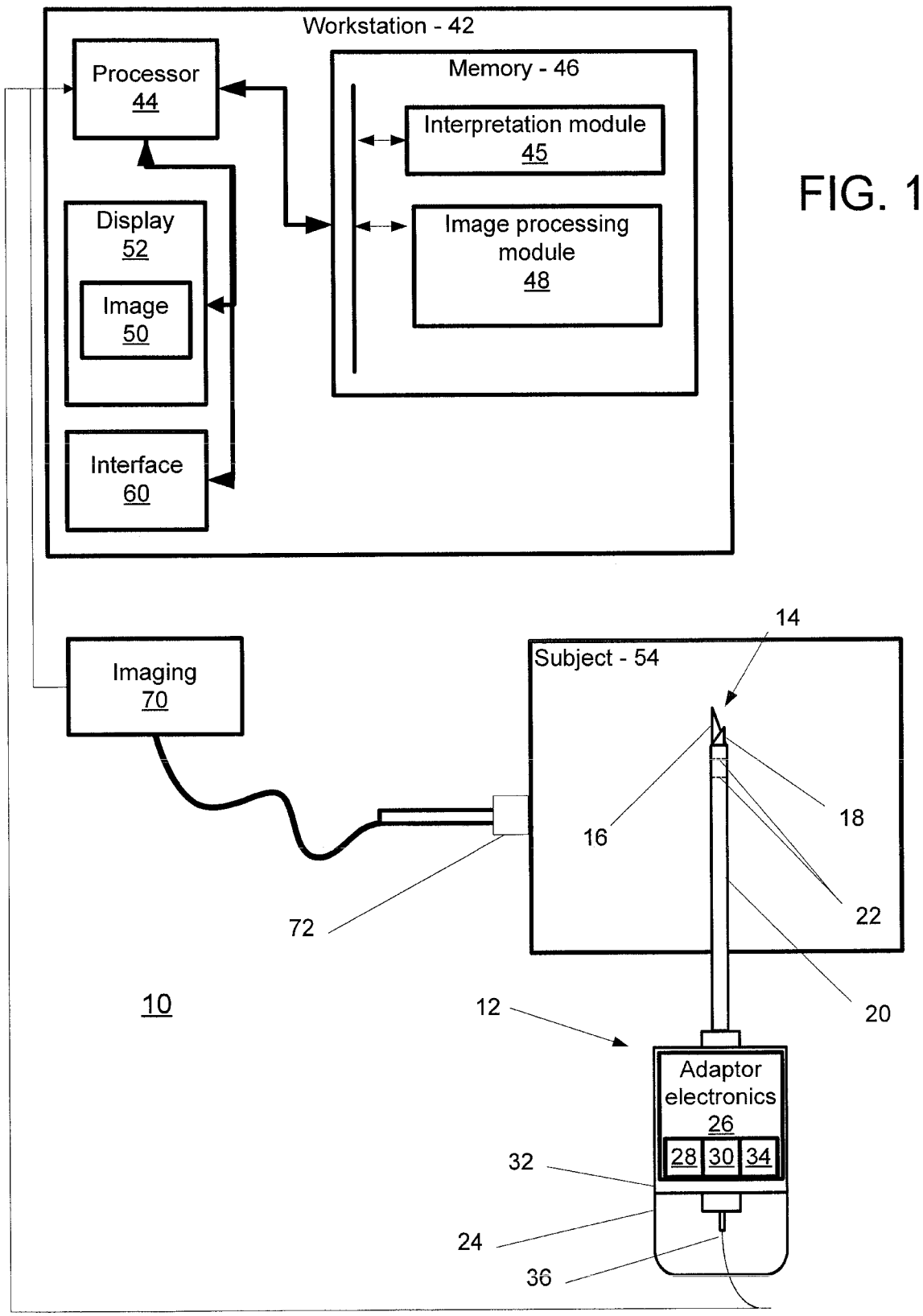
FIG. 1 is a schematic block/flow diagram showing a system for tracking a medical device which includes sensors in an introducer in accordance with one embodiment.

In accordance with the present principles, a biopsy introducer is provided that includes one or more ultrasound sensors. The introducer may include disposable and/or non-disposable configurations. In one embodiment, an interface clip is provided that attaches the introducer to a biopsy gun handle. The exemplary interface clip can be configured to retrofit multiple biopsy gun handles in an ergonomic manner. For example, in accordance with exemplary embodiments, an interface clip can be non-disposable (e.g., reusable) and/or disposable. In an exemplary non-disposable version, the interface clip can include adaptor electronics (e.g., amplifying and noise-cancelling electronics). The exemplary introducer in this case can be either non-disposable or disposable.

In accordance with another exemplary embodiment, the interface clip can be disposable. In such a case, the exemplary introducer and interface clip can be combined into a single hardware design (device), since they can both be disposable. The interface clip does not need to include the adaptor electronics, as the adaptor electronics can be housed separately. Benefits of exemplary embodiments can include, but are not limited to, no requirement to sterilize the adaptor, since, e.g., the adaptor may not come in contact with the patient. In one embodiment, the interface clip can be attached to the biopsy gun handle. Other embodiments can be commercialized independently and made compatible with multiple disposable biopsy needles on the market.

In accordance with exemplary embodiments, dedicated hardware can be employed to enable cost-effective tracking of a needle or other device. InSitu technology can be utilized for biopsy procedures, without modifying the biopsy gun design. InSitu technology can be employed with commercially available biopsy guns, for example. A modular design can interface with the biopsy gun using a combination of non-disposable and/or disposable hardware to employ.

It should be understood that the present invention will be described in terms of medical instruments; however, the teachings of the present invention are much broader and are applicable to any trackable instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Further, it should be understood that any new computer-readable medium which may hereafter be developed should also be considered as computer-readable medium as may be used or referred to in accordance with exemplary embodiments of the present invention and disclosure.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as, e.g., a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, an illustrative biopsy system 10 is shown in accordance with one embodiment. The system 10 includes a biopsy gun 12 configured for needle tracking. The biopsy gun 12 includes a biopsy needle 14 having an inner stylet 16 disposed within an outer cannula 18. The needle 14 is in turn disposed within an introducer 20. The introducer 20 encapsulates the needle 14. The introducer 20 includes one or more tracking sensors 22. The tracking sensors 22 may include ultrasonic sensors although other types of sensors may be employed for tracking the needle 14.

In one embodiment, the introducer 20 is connected with an interface 32. The interface 32 connects the introducer 20 to a biopsy gun handle 24. The interface 32 may include adaptor electronics 26 therein. The adaptor electronics 26 may include noise cancellation modules 28 (software and/or hardware), amplifiers 30 and any another signal processing modules 34 needed to process received signals from sensors 22.

The sensors 22 function as ultrasound trackers. The introducer 20 and the sensors 22 may be disposable or non-disposable. In one embodiment, the ultrasound trackers for sensors 22 may include PZT, PVDF, or other piezoelectric element disposed between conductive plates or layers. The interface or interface clip 32 may be employed to attach the introducer 20 to the biopsy gun handle 24. The interface 32 may include the adaptor electronics 26 and be reusable (non-disposable). In another embodiment, the interface 32 may be made disposable. In another embodiment, the introducer 20 and interface 32 can be combined into a single disposable device. A sensor cable 36 can be provided (although wireless connections are also contemplated) as an output from the interface 32 and can be connected to an adaptor or other connector. The interface 32 may be reusable (non-disposable).

In one embodiment, the introducer 20 includes a hollow tube including one or more ultrasound trackers or sensors 22 that can be tracked using InSitu technology. The introducer 20 may have an inner diameter that is marginally thicker than the cannula 18, thereby permitting the cannula 18 and the stylet 16 to fit inside the introducer 20. The length of the introducer 20 can be approximately equal to the length of the needle 16 in its resting position prior to firing. If at least two sensors 22 are employed, the orientation of the introducer 20 (and also the cannula 18 and stylet 16) can be estimated. Therefore, the biopsy location coordinates can be computed prior to firing.

The biopsy system 10 may work in conjunction with or be integrated in a workstation or console 42 from which a procedure is supervised and/or managed. Workstation 42 preferably includes one or more processors 44 and memory 46 for storing programs and applications. Memory 46 may store an interpretation module 45 configured to interpret feedback signals from sensors 22. Interpretation module 45 is configured to employ the signal feedback (and any other feedback, e.g., electromagnetic (EM) tracking) to reconstruct position and orientation of the introducer 20 or other medical device or instrument. The other medical devices may include a catheter, a guidewire, a probe, an endoscope, a robot, an electrode, a filter device, a balloon device, or other medical component, etc.

In one embodiment, workstation 42 includes an image processing module 48 configured to receive feedback from the sensors 22 and further process the information to determine position and orientation of the introducer 20 within a volume (subject) 54. An image 50 for the space or volume 54 can be generated and displayed on a display device 52 that indicates the position and orientation of the introducer 20 (and other components) in a live image.

Interpretation module 45 can also be configured to determine an estimated position of where a biopsy sample will be taken in the subject 54. The interpretation module 45 may convey this information to the image processing module 48 to generate an image showing a location of the estimated position to assist a user. The image may include a line or other shape to provide a visual indicator (see FIG. 2, estimated position 104).

Workstation 42 includes the display 52 for viewing internal images of a subject (patient) or volume 54 and may include the image as an overlay or other rendering of the sensors 22, introducer 20, needle 14, etc. Display 52 may also permit a user to interact with the workstation 42 and its components and functions, or any other element within the system. This is further facilitated by an interface 60 which may include a keyboard, mouse, a joystick, a haptic device, or any other peripheral or control to permit user feedback from and interaction with the workstation 42.

An imaging system 70 is provided for imaging the introducer 20 for guidance and positioning. In one embodiment, the imaging system 70 includes an ultrasound imaging system, which employs an imaging probe 72. The imaging probe 72 provides ultrasonic energy, which is received by the sensors 20. The sensors 20 are electrically connected (by wires, not shown, or wirelessly) to the adaptor electronics 26 for signal processing and amplification. The adaptor electronics 26 may in turn be connected to the workstation 42 where the interpretation module 45 further processes the signals, registers the introducer 20 (and other components) to the images collected by the imaging system 70. While the imaging system 70 is described as an ultrasound imaging system 70, other imaging technologies may be employed.

Figure 2:
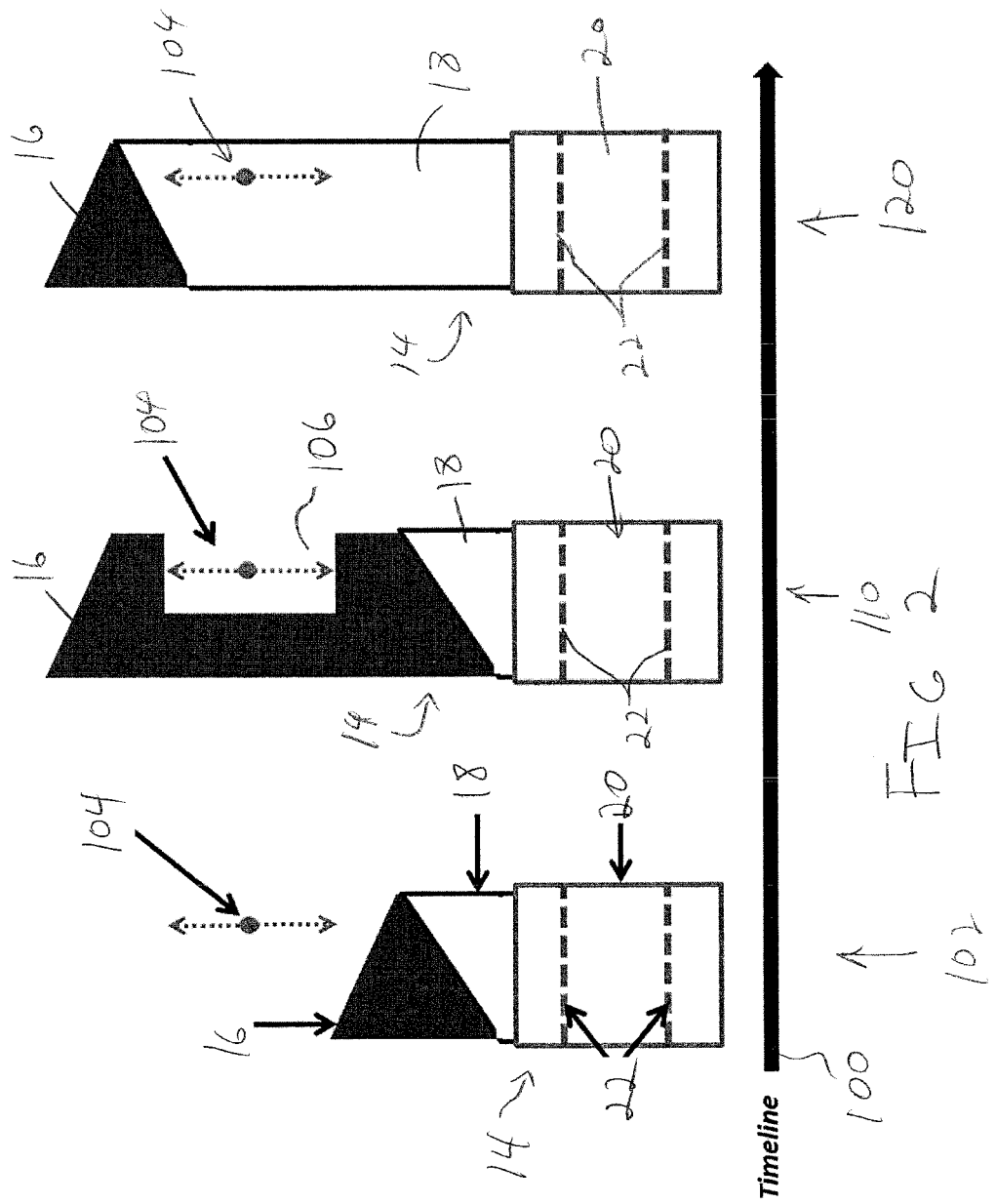
FIG. 2 is a timeline and diagram showing a system for tracking a medical device with sensors in an introducer at three instances: before firing, after firing an inner stylet and after firing an outer cannula in accordance with one embodiment.

Referring to FIG. 2, an illustrative timeline 100 is shown for a biopsy procedure that employs the introducer with sensors in accordance with the present principles. In a first instance 102, a biopsy needle 14 is loaded in a ready-to-fire position. Using two or more sensors 22 on the introducer 20, the orientation of the introducer 20 and therefore the needle 14 will be known. An estimated biopsy location 104 may be determined based upon the needle/introducer orientation and a known throw of the inner stylet 16 relative to the outer cannula 18. In other words, the estimated location 104 can easily be estimated using the positions of the sensors 22 as a baseline and adding the throw of the inner stylet 16 in the direction of the introducer 20. The estimated biopsy location 104 may be indicated in an image to assist the user.

The sensors 22 may include ultrasound sensors. In this case, an ultrasound probe transmits signals that are received by the sensors 22. Using time of flight information and knowledge of the coordinate system of the subject, positions of the sensors 22 (and therefore introducer 20 and the needle 14) can be determined in the ultrasound space and the estimated location 104 determined.

In a second instance 110, the inner stylet 16 is fired. The inner stylet 16 rapidly advances to the throw extent to capture a biopsy sample in a chamber 106 of the inner stylet 16 that corresponds with the estimated position 104. In a third instance 120, the outer cannula 18 is advanced to shear off the biopsy sample in the chamber 106 and enclose the chamber 106 to safely remove the biopsy sample from the subject.

Figure 3:
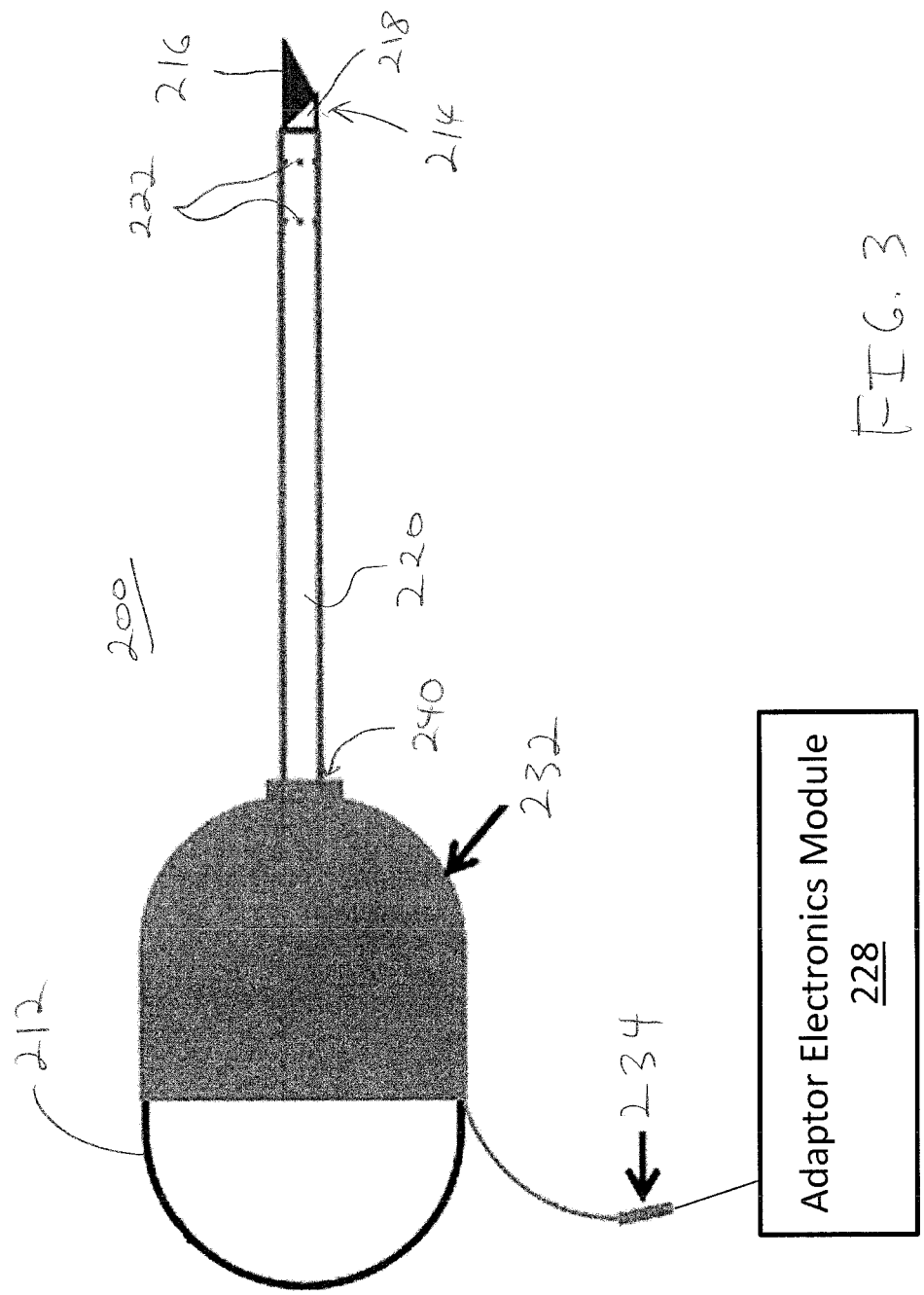
FIG. 3 is a schematic block/flow diagram showing a system for tracking a medical device where an interface does not include adaptor electronics and is disposable in accordance with one embodiment.

Referring to FIG. 3, another embodiment of a biopsy system 200 is illustratively shown. Biopsy system 200 includes a disposable interface 232. The interface 232 is attached to an introducer 220 such that the interface 232 and the introducer 220 are removable and disposable from a biopsy gun handle 212.

The biopsy gun 212 is configured for needle tracking. The biopsy gun 212 includes a biopsy needle 214 having an inner stylet 216 disposed within an outer cannula 218 as described above. The needle 214 is, in turn, disposed within the introducer 220, which may include a hollow tube introducer 220 to encapsulate the needle 214. The introducer 220 includes one or more tracking sensors 222 (e.g., on the inside diameter of the tube, although the sensors 222 may be mounted on an exterior of the introducer 220). The tracking sensors 222 may include ultrasonic sensors although other types of sensors may be employed for tracking the needle 214.

In one embodiment, the introducer 220 may be integrally formed with the interface 232 or the interface 232 may be a separate part that connects to the introducer 220. The interface 232, since it is disposable, may or may not include adaptor electronics therein. The adaptor electronics may be included in a separate module 228 for noise cancellation, amplifiers, etc. to process received signals from sensors 222.

The sensors 222 may include one or more ultrasound trackers. The introducer 220 and the sensors 222 may be disposable. In one embodiment, the ultrasound trackers for sensors 222 may include PZT, PVDF, or other piezoelectric element disposed between conductive plates or layers. The interface 232 may be employed to attach the introducer 220 to the biopsy gun handle 224. The interface 232 may include the adaptor electronics and be reusable (non-disposable), although a disposable embodiment may include a reusable adaptor electronics module 228. In this instance, the interface 232 is disposable and the adaptor electronics 228 are not disposable. A cable 234 can be provided as an output from the sensors 222 and can be connected to the adaptor electronics module 228 or other connector or system, e.g., a system employing InSitu technology (see e.g., FIG. 1).

The interface 232 may include an opening 240 to receive the introducer 220. When the introducer 220 is fitted into the interface 232, an electrical connection is completed between a wire or wires of the sensors 220 through the introducer 220 and to the cable 234 from the interface 232. The introducer 220 can be disposable or non-disposable with the sensors 222 and their wiring. The adaptor electronics can then be housed separately (module 228) so that it does not come in contact with the subject (e.g., the patient).

Referring again to FIG. 1 with continued reference to FIG. 3, the use of ultrasound tracking technology (InSitu) can be utilized to more accurately estimate a true location of the biopsy sample. For example, InSitu technology can be used to estimate the position of a passive ultrasound sensor (e.g., PZT, PVDF, copolymer or other piezoelectric material) in a field of view (FOV) of a diagnostic B-mode image by analyzing a signal received by a sensor as beams of the imaging probe sweep the FOV. Time-of-flight measurements can be used to provide the axial/radial distance of the sensor 22 (FIG. 1) or 222 from the imaging array of the ultrasound system, while amplitude measurements and knowledge of the beam firing sequence can be used to provide (or determine) the lateral/angular position of the sensor 22, 222. When used with 3D transducers (e.g., 2D matrix arrays) (US imaging probe), the elevational position of the sensor 22, 222 can also be obtained in a similar manner. Therefore, the 3D position of the sensor 22, 222 can be estimated in real-time, provided it is present within the FOV of the imaging transducer.

The sensors 22, 222 on the introducer 20, 220 passively listen to the ultrasound waves impinging on them as the imaging probe's beams sweep the field of view. Analysis of these signals yields the position of the sensor 22, 222 on the introducer 20, 220 in the frame of reference of the ultrasound image. The position can then be overlaid on an ultrasound image for enhanced visualization, and the positions and their histories can be logged for tracking, segmentation, and other applications.

Embodiments in accordance with the present principles can be made compatible with multiple biopsy needles on the market. In addition, the introducers described herein may be employed in procedures other than biopsy procedures. For example, the present principles may be employed for ablation needle guidance, catheter guidance, endoscopic procedures, etc. Moreover, it is contemplated that corresponding and/or related systems incorporating and/or implementing the present principles are also contemplated and considered to be within the scope of the present invention. Further, corresponding and/or related methods for manufacturing and/or using a device and/or system in accordance with the present disclosure are also contemplated and considered to be within the scope of the present invention.

Figure 4:
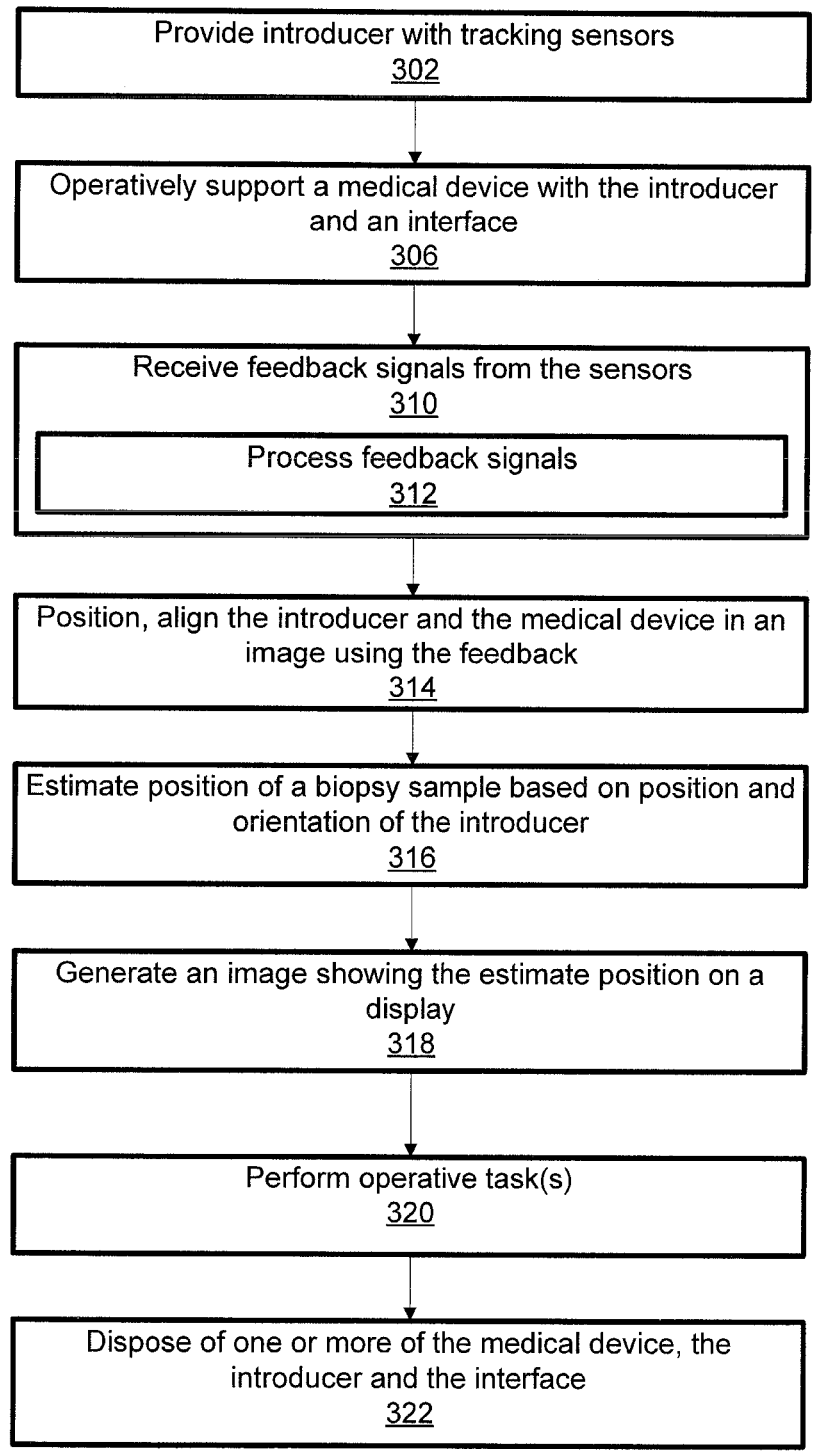
FIG. 4 is a flow diagram showing a method for tracking a medical device in accordance with an illustrative embodiment.

Referring to FIG. 4, a method for tracking a medical device is illustratively shown. In block 302, an introducer is provided with two or more sensors disposed along a length of the introducer. The sensors are spaced apart from adjacent sensors along the introducer to assist in providing position and orientation information for tracking the introducer. The introducer is coupled to an interface at one end portion. In block 306, the medical device is operatively supported by the introducer and the interface. This means that, e.g., if the medical device includes a biopsy needle, the needle fits within the introducer and is operable (e.g., can be fired) from the introducer. In addition, the interface supports the introducer by providing a mechanical support between the biopsy gun and the introducer. Other configurations are also contemplated.

In block 310, signals are received from a subject by the two or more sensors, which are configured to provide feedback for positioning and orienting the medical device in a medical image. In block 312, the feedback signals are processed using adaptor electronics configured to connect to the sensors and provide noise cancellation, amplify the signals, filter the signals, etc.

In block 314, the introducer and therefore the medical device is positioned in a field of view of an image and aligned with a biopsy sample or other target using the feedback signals.

In block 316, the medical device may include a biopsy gun including a needle with an inner stylet and an outer cannula. An estimate position of a biopsy sample may be determined based upon a position and orientation of the introducer. The estimate position may be manually determined or may be computed using an interpretation module (FIG. 1). In block 318, an image may be generated on a display to show the estimate position based upon the position and orientation of the introducer. The image may include an indicator, such as an arrow, shape, line, etc. or may include an overlay or a virtual image.

In block 320, operative tasks are performed, for example, fire the biopsy gun, take the biopsy sample, etc. In block 322, one or more of the introducer, the interface, the medical instrument may be disposed. In one embodiment, the introducer is disposable and the interface is reusable. In another embodiment, the introducer and the interface are disposed of as a single unit or integrated assembly. The interface may or may not include adaptor electronics.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for ultrasound tracking apparatus for disposable biopsy needles (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

What is claimed is:

1. A system for tracking a needle of a disposable biopsy gun having a handle, the system comprising:
   an introducer configured as a hollow tube to receive the needle of the biopsy gun within the hollow tube;
   two or more sensors disposed along a length of the introducer and being spaced apart along the length, each of the sensors include an electrical connector; and
   an interface clip configured to connect to the introducer and the introducer and the interface clip configured to operatively couple to and at least mechanically support the biopsy gun, and the interface clip configured to: (i) removably attach to the handle of the biopsy gun and (ii) electrically couple the electrical connector of each sensor to adaptor electronics configured to adapt a signal from the sensors,
   wherein the two or more sensors are configured to provide feedback for positioning and orienting the biopsy gun using medical imaging.

2. The system as recited in claim 1, wherein the sensors are disposed within the hollow tube.

3. The system as recited in claim 1, wherein the introducer connects to the interface clip and at least one of the introducer and the interface clip is disposable.

4. The system as recited in claim 1, wherein the introducer is integrated with the interface clip to form an assembly and the assembly is disposable.

5. The system as recited in claim 1, wherein the adaptor electronics are configured to provide amplification, noise cancellation, and/or other adaptive signal processing to the signal from the sensors.

6. The system as recited in claim 5, wherein the adaptor electronics are integrated as a physical part of the interface clip.

7. The system as recited in claim 6, wherein the interface clip defines and surrounds an opening, wherein the opening is configured to receive and fit the introducer.

8. The system as recited in claim 5, wherein further adaptor electronics are included in a module external to the interface clip.

9. A system for tracking a needle of a disposable biopsy gun having a handle, the system comprising:
   an introducer configured as a hollow tube to receive the needle of the biopsy gun within the hollow tube;
   two or more sensors disposed along a length of the introducer and being spaced apart along the length, each of the sensors include an electrical connector;
   an interface clip configured to connect to the introducer with the introducer and the interface clip configured to operatively couple to and at least mechanically support the biopsy gun, and the interface clip configured to (i) removably attach to the handle of the biopsy gun and (ii) electrically couple the electrical connector of each sensor to adaptor electronics configured to adapt a signal from the sensors,
   wherein the two or more sensors are configured to provide feedback for positioning and orienting the biopsy gun; and
   an interpretation module configured to receive the feedback, adapted by the adaptor electronics, and generate image information for indicating a position and orientation of the needle in an image.

10. The system as recited in claim 9, wherein the sensors are disposed within the hollow tube.

11. The system as recited in claim 9, wherein at least one of the introducer and the interface clip is disposable.

12. The system as recited in claim 9, wherein the introducer is integrated as a physical part of the interface clip to form an assembly and the assembly is disposable.

13. The system as recited in claim 12, wherein the interface clip defines and surrounds an opening, wherein the opening is configured to receive and fit the introducer.

14. The system as recited in claim 9, wherein the adaptor electronics are configured to provide amplification, noise cancellation, and/or other adaptive signal processing to the signal from the sensors prior to being received by the interpretation module.

15. A method for tracking a needle of a disposable biopsy gun having a handle, the method comprising:
   providing an introducer with two or more sensors disposed along a length of the introducer and being spaced apart along the length, the introducer being coupled to an interface clip, the introducer being configured as a hollow tube to receive the needle of the biopsy gun within the hollow tube, and each of the sensors including an electrical connector;
   operatively coupling and at least mechanically supporting the biopsy gun by the introducer and the interface clip with the interface clip (i) removably attaching to the handle of the biopsy gun and (ii) electrically coupling the electrical connector of each sensor to adapter electronics configured to adapt a signal from the sensors,
   receiving signals from a subject by the two or more sensors which are configured to provide feedback for positioning and orienting the biopsy gun in a medical image.

16. The method as recited in claim 15, wherein the adaptor electronics are configured to provide amplification, noise cancellation, and/or other adaptive signal processing to the signal from the sensors.

17. The method as recited in claim 15, wherein the introducer is integrated as a physical part of the interface clip to form an assembly and the assembly is disposable.

18. The method as recited in claim 17, wherein providing the interface clip comprises configuring the interface clip to define and surround an opening that is configured to receive and fit the introducer.

19. The method as recited in claim 15, wherein the needle includes an inner stylet and an outer cannula, and the method further comprises determining an estimated position of a biopsy sample based upon a position and orientation of the introducer.

20. The method as recited in claim 19, further comprising generating an image of the estimated position based upon the position and orientation of the introducer.

* * * * *